United States Patent
Bodnar et al.

(10) Patent No.: US 9,693,943 B1
(45) Date of Patent: Jul. 4, 2017

(54) COMPOSITIONS CONTAINING COMBINATIONS OF SUNSCREEN ACTIVE AGENTS

(71) Applicant: L'ORÉAL, Paris (FR)

(72) Inventors: Brian Scott Bodnar, Manasquan, NJ (US); Omotayo Awofesobi, West Orange, NJ (US); Anil Shah, East Windsor, NJ (US)

(73) Assignee: L'ORÉAL, Paris (FR)

( * ) Notice: Subject to any disclaimer, the term of this patent is extended or adjusted under 35 U.S.C. 154(b) by 0 days.

(21) Appl. No.: 14/985,168

(22) Filed: Dec. 30, 2015

(51) Int. Cl.
*A61K 8/72* (2006.01)
*A61K 8/81* (2006.01)
*A61Q 17/04* (2006.01)
*A61K 8/40* (2006.01)
*A61K 8/37* (2006.01)
*A61K 8/19* (2006.01)

(52) U.S. Cl.
CPC .................. *A61K 8/40* (2013.01); *A61K 8/19* (2013.01); *A61K 8/37* (2013.01); *A61Q 17/04* (2013.01); *A61K 2800/5922* (2013.01)

(58) Field of Classification Search
CPC .. A61K 2800/52; A61K 2800/59; A61K 8/35; A61K 8/40; A61Q 17/04
See application file for complete search history.

(56) References Cited

U.S. PATENT DOCUMENTS

| | | | |
|---|---|---|---|
| 8,545,891 B1 | 10/2013 | Halpern et al. | |
| 8,557,227 B2 | 10/2013 | Simonnet et al. | |
| 8,652,449 B1 | 2/2014 | Halpern et al. | |
| 8,691,192 B1 | 4/2014 | Halpern et al. | |
| 9,107,843 B2 | 8/2015 | Simonnet et al. | |
| 9,132,074 B2 | 9/2015 | Halpern et al. | |
| 9,138,395 B2 | 9/2015 | Halpern et al. | |
| 9,138,396 B2 | 9/2015 | Halpern et al. | |
| 2004/0126337 A1* | 7/2004 | Singleton | A61Q 17/04 424/59 |
| 2009/0035234 A1 | 2/2009 | Cunningham et al. | |
| 2009/0098070 A1 | 4/2009 | Karpov et al. | |
| 2012/0039827 A1* | 2/2012 | Chaudhuri | A61K 8/347 424/59 |
| 2013/0129649 A1 | 5/2013 | Simonnet et al. | |
| 2013/0243709 A1 | 9/2013 | Hanson et al. | |
| 2014/0030198 A1 | 1/2014 | Fares et al. | |

FOREIGN PATENT DOCUMENTS

WO  WO2008/042326  4/2008

OTHER PUBLICATIONS

International Search Report issued Mar. 13, 2017 in PCT/US2016/063822.
Written Opinion of the International Searching Authority issued Mar. 13, 2017 in PCT/US2016/063822.

* cited by examiner

*Primary Examiner* — Alma Pipic

(74) *Attorney, Agent, or Firm* — Oblon, McClelland, Maier & Neustadt, L.L.P.

(57) ABSTRACT

Compositions containing octocrylene, octinoxate, octisalate, homosalate and having improved sun protection factor (SPF) properties, as well as methods of improving sun protection factor (SPF) properties of compositions, are provided.

20 Claims, No Drawings

COMPOSITIONS CONTAINING COMBINATIONS OF SUNSCREEN ACTIVE AGENTS

FIELD OF THE INVENTION

The present invention relates to compositions containing combinations of sunscreen active agents and having improved sun protection factor (SPF) properties.

BACKGROUND OF THE INVENTION

Compositions containing sunscreen active agents are highly popular. Sunscreen active agents in such compositions protect keratinous material such as hair and skin from the harm caused by UV radiation, including harm from both UVA and UVB rays. A standard measure for determining the amount of protection a composition containing sunscreen active agent provides against UV radiation, particularly against UVB rays, is sun protection factor (SPF). However, given the finite amount of approved sunscreen active agents worldwide, increasing SPF of compositions containing sunscreen active agents can be difficult.

US patent application 2013/0129649 refers to a mixture of sunscreens which cannot be used in conjunction with oxides such as titanium dioxide and zinc oxide (namely avobenzone) and to specific ratios of specific sunscreen active agents. Other combinations of sunscreen active agents include those disclosed in U.S. Pat. No. 8,545,891, U.S. Pat. No. 8,557,227, U.S. Pat. No. 8,652,449, U.S. Pat. No. 8,691,192, U.S. Pat. No. 9,107,843, U.S. Pat. No. 9,132,074, U.S. Pat. No. 9,138,395, U.S. Pat. No. 9,138,396 and WO 2008042326.

Accordingly, one aspect of the present invention are compositions containing a combination of sunscreen active agents and having improved sun protection factor (SPF) properties. Other aspects of the present invention are methods of improving sun protection factor (SPF) properties of compositions containing sunscreen active agents and methods of preparing stable sunscreen compositions containing sunscreen active agents and metal oxides.

SUMMARY OF THE INVENTION

The present invention relates to compositions for keratinous materials (for example, hair or skin) comprising octocrylene, octinoxate, octisalate, homosalate, wherein the compositions contain all of the following weight ratios:
Octocrylene to Homosalate: from 3:1 to 4.5:1;
Octinoxate to Octisalate: from 1.5:1 to 1:1.5;
Octocrylene to Octinoxate: from 2.5:1 to 1.1:1; and
Octocrylene to Octisalate: from 2.5:1 to 1.25:1.

The present invention also relates to compositions for keratinous materials (for example, hair or skin) comprising octocrylene, octinoxate, octisalate, homosalate and at least one metal oxide, wherein the compositions contain all of the following weight ratios:
Octocrylene to Homosalate: from 3:1 to 4.5:1;
Octinoxate to Octisalate: from 1.5:1 to 1:1.5;
Octocrylene to Octinoxate: from 2.5:1 to 1.1:1; and
Octocrylene to Octisalate: from 2.5:1 to 1.25:1.

The present invention further relates to compositions for keratinous materials (for example, hair or skin) comprising octocrylene, octinoxate, octisalate, homosalate, wherein the compositions contain all of the following weight ratios:
Octocrylene:Octinoxate:Octisalate:Homosalate: about 4.5:about 2:about 2:about 1.5.

The present invention also relates to compositions for keratinous materials (for example, hair or skin) comprising octocrylene, octinoxate, octisalate, homosalate and at least one metal oxide, wherein the compositions contain all of the following weight ratios:
Octocrylene:Octinoxate:Octisalate:Homosalate: about 4.5:about 2:about 2:about 1.5.

The present invention further relates to compositions for keratinous materials (for example, hair or skin) comprising octocrylene, octinoxate, octisalate, homosalate and a sunscreen effective amount of at least one metal oxide selected from the group consisting of zinc oxide, titanium dioxide, and mixtures thereof, wherein the compositions contain all of the following weight ratios of octocrylene, octinoxate, octisalate and homosalate:
Octocrylene to Homosalate: from 3:1 to 4.5:1;
Octinoxate to Octisalate: from 1.5:1 to 1:1.5;
Octocrylene to Octinoxate: from 2.5:1 to 1.1:1; and
Octocrylene to Octisalate: from 2.5:1 to 1.25:1.

The present invention also relates to compositions for keratinous materials (for example, hair or skin) comprising octocrylene, octinoxate, octisalate, homosalate and a sunscreen effective amount of at least one metal oxide selected from the group consisting of zinc oxide, titanium dioxide, and mixtures thereof, wherein the compositions contain all of the following weight ratios of octocrylene, octinoxate, octisalate and homosalate:
Octocrylene:Octinoxate:Octisalate:Homosalate: about 4.5:about 2:about 2:about 1.5.

The present invention also relates to methods of increasing the sun protection factor (SPF) properties of a composition comprising adding octocrylene, octinoxate, octisalate, homosalate, to the composition in all of the following weight ratios of octocrylene, octinoxate, octisalate and homosalate:
Octocrylene to Homosalate: from 3:1 to 4.5:1;
Octinoxate to Octisalate: from 1.5:1 to 1:1.5;
Octocrylene to Octinoxate: from 2.5:1 to 1.1:1; and
Octocrylene to Octisalate: from 2.5:1 to 1.25:1.

The present invention further relates to methods of increasing the sun protection factor (SPF) properties of a composition comprising adding octocrylene, octinoxate, octisalate, homosalate and at least one metal oxide, to the composition in all of the following weight ratios of octocrylene, octinoxate, octisalate and homosalate:
Octocrylene to Homosalate: from 3:1 to 4.5:1;
Octinoxate to Octisalate: from 1.5:1 to 1:1.5;
Octocrylene to Octinoxate: from 2.5:1 to 1.1:1; and
Octocrylene to Octisalate: from 2.5:1 to 1.25:1.

The present invention also relates to methods of increasing the sun protection factor (SPF) properties of a composition comprising adding octocrylene, octinoxate, octisalate, homosalate, to the composition in all of the following weight ratios of octocrylene, octinoxate, octisalate and homosalate:
Octocrylene:Octinoxate:Octisalate:Homosalate: about 4.5:about 2:about 2:about 1.5.

The present invention also relates to methods of increasing the sun protection factor (SPF) properties of a composition comprising adding octocrylene, octinoxate, octisalate, homosalate and at least one metal oxide, to the composition in all of the following weight ratios of octocrylene, octinoxate, octisalate and homosalate:
Octocrylene:Octinoxate:Octisalate:Homosalate: about 4.5:about 2:about 2:about 1.5.

The present invention also relates to methods of increasing the sun protection factor (SPF) properties of a composition comprising adding octocrylene, octinoxate, octisalate, homosalate and a sunscreen effective amount of at least one metal oxide selected from the group consisting of zinc oxide, titanium dioxide, and mixtures thereof, to the composition in all of the following weight ratios of octocrylene, octinoxate, octisalate and homosalate:

Octocrylene to Homosalate: from 3:1 to 4.5:1;
Octinoxate to Octisalate: from 1.5:1 to 1:1.5;
Octocrylene to Octinoxate: from 2.5:1 to 1.1:1; and
Octocrylene to Octisalate: from 2.5:1 to 1.25:1.

The present invention also relates to methods of increasing the sun protection factor (SPF) properties of a composition comprising adding octocrylene, octinoxate, octisalate, homosalate and a sunscreen effective amount of at least one metal oxide selected from the group consisting of zinc oxide, titanium dioxide, and mixtures thereof, to the composition in all of the following weight ratios of octocrylene, octinoxate, octisalate and homosalate:

Octocrylene:Octinoxate:Octisalate:Homosalate: about 4.5: about 2:about 2:about 1.5.

It is to be understood that both the foregoing general description and the following detailed description are exemplary and explanatory only, and are not restrictive of the invention.

DETAILED DESCRIPTION OF THE INVENTION

Other than in the operating examples, or where otherwise indicated, all numbers expressing quantities of ingredients and/or reaction conditions are to be understood as being modified in all instances by the term "about."

In the following description of the invention and the claims appended hereto, it is to be understood that the terms used have their ordinary and accustomed meanings in the art, unless otherwise specified.

"About" as used herein means within 10% of the indicated number (e.g. "about 10%" means 9%-11% and "about 2%" means 1.8%-2.2%).

"A" or "an" as used herein means "at least one."

As used herein, all ranges provided are meant to include every specific range within, and combination of subranges between, the given ranges. Thus, a range from 1-5, includes specifically 1, 2, 3, 4 and 5, as well as subranges such as and 2-5, 3-5, 2-3, 2-4, 1-4, etc.

"Substituted" as used herein, means comprising at least one substituent. Non-limiting examples of substituents for substitution include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Volatile", as used herein, means having a flash point of less than about 100° C.

"Non-volatile", as used herein, means having a flash point of greater than about 100° C.

"Physiologically acceptable medium" is means a medium that is compatible with human keratin materials, for instance the skin, the lips, the nails, the eyelashes, the eyebrows or the hair.

"Cosmetic composition" means a composition that is compatible with keratin materials. The composition of the present invention may be in any form, either liquid or nonliquid (semi-solid, soft solid, solid, etc.). For example, it may be a paste, a solid, a gel, or a cream. It may be anhydrous. It may be an emulsion, such as an oil-in-water or water-in-oil emulsion, a multiple emulsion, such as an oil-in-water-in-oil emulsion or a water-in-oil-in-water emulsion, or a solid, rigid or supple gel. The composition of the invention may, for example, comprise an external or continuous fatty phase. The composition can also be a molded composition or cast as a stick or a dish.

Depending on the intended application, such as a stick, hardness of the composition may also be considered. The hardness of a composition may, for example, be expressed in gramforce (gf). The composition of the present invention may, for example, have a hardness ranging from 20 gf to 2000 gf, such as from 20 gf to 900 gf, and further such as from 20 gf to 600 gf.

This hardness is measured in one of two ways. A first test for hardness is according to a method of penetrating a probe into the composition and in particular using a texture analyzer (for example TA-XT2i from Rheo) equipped with an ebonite cylinder of height 25 mm and diameter 8 mm. The hardness measurement is carried out at 20° C. at the center of 5 samples of the composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed. The measurement error is ±50 gf.

The second test for hardness is the "cheese wire" method, which involves cutting an 8.1 mm or preferably 12.7 mm in diameter stick composition and measuring its hardness at 20° C. using a DFGHS 2 tensile testing machine from Indelco-Chatillon Co. at a speed of 100 mm/minute. The hardness value from this method is expressed in grams as the shear force required to cut a stick under the above conditions. According to this method, the hardness of compositions according to the present invention which may be in stick form may, for example, range from 30 gf to 300 gf, such as from 30 gf to 250 gf, for a sample of 8.1 mm in diameter stick, and further such as from 30 gf to 200 gf, and also further such as from 30 gf to 120 gf for a sample of 12.7 mm in diameter stick.

The hardness of the composition of the present invention may be such that the compositions are self-supporting and can easily disintegrate to form a satisfactory deposit on keratin materials. In addition, this hardness may impart good impact strength to the inventive compositions, which may be molded or cast, for example, in stick or dish form.

The skilled artisan may choose to evaluate a composition using at least one of the tests for hardness outlined above based on the application envisaged and the hardness desired. If one obtains an acceptable hardness value, in view of the intended application, from at least one of these hardness tests, the composition falls within preferred embodiments of the invention.

"Keratin materials" means the skin (body, face, contour of the eyes, scalp), head hair, eyelashes, eyebrows, bodily hairs, nails and/or lips.

The compositions and methods of the present invention can comprise, consist of, or consist essentially of the essential elements and limitations of the invention described herein, as well as any additional or optional ingredients, components, or limitations described herein or otherwise useful.

Referred to herein are trade names for materials including, but not limited to polymers and optional components. The inventors herein do not intend to be limited by materials described and referenced by a certain trade name. Equivalent materials (e.g., those obtained from a different source under a different name or catalog (reference) number) to those referenced by trade name may be substituted and utilized in the methods described and claimed herein.

All percentages and ratios are calculated by weight unless otherwise indicated. All percentages are calculated based on the total weight of a composition unless otherwise indicated. All component or composition levels are in reference to the active level of that component or composition, and are exclusive of impurities, for example, residual solvents or by-products, which may be present in commercially available sources.

Compositions of the Present Invention

According to the present invention, compositions comprising octocrylene, octinoxate, octisalate, homosalate, wherein the compositions contain all of the following weight ratios of octocrylene, octinoxate, octisalate and homosalate:
Octocrylene to Homosalate: from 3:1 to 4.5:1;
Octinoxate to Octisalate: from 1.5:1 to 1:1.5;
Octocrylene to Octinoxate: from 2.5:1 to 1.1:1; and
Octocrylene to Octisalate: from 2.5:1 to 1.25:1,
are provided. According to preferred embodiments, the compositions contain all of the following weight ratios of octocrylene, octinoxate, octisalate and homosalate:
Octocrylene:Octinoxate:Octisalate:Homosalate: about 4.5: about 2:about 2:about 1.5.

Homosalate is available, for example, as "510133 NEO Heliopan HMS PBF" from Symrise; octisalate (also known as ethylhexyl salicylate) is available, for example, as "Neo Heliopan OS/H" from Symrise; octocrylene is available, for example, as "Escalol 597" from Ashland; and octinoxate (also known as ethylhexyl methoxycinnamate) is available, for example, as "Escalol 557" from Ashland.

Preferably, octocrylene, octinoxate, octisalate and homosalate are present in the compositions according to the invention in a combined amount ranging from about 5% to about 50% by weight with respect to the total weight of the composition, preferably ranging from about 6 to about 40% by weight with respect to the total weight of the composition, preferably ranging from about 7 to about 30% by weight with respect to the total weight of the composition, preferably ranging from about 8 to about 20% by weight with respect to the total weight of the composition, preferably ranging from about 9 to about 15% by weight with respect to the total weight of the composition, including all ranges and subranges therebetween.

Metal Oxides

According to the present invention, compositions comprising octocrylene, octinoxate, octisalate, homosalate and at least one metal oxide, wherein the compositions contain all of the following weight ratios of octocrylene, octinoxate, octisalate and homosalate:
Octocrylene to Homosalate: from 3:1 to 4.5:1;
Octinoxate to Octisalate: from 1.5:1 to 1:1.5;
Octocrylene to Octinoxate: from 2.5:1 to 1.1:1; and
Octocrylene to Octisalate: from 2.5:1 to 1.25:1,
are provided. According to preferred embodiments, the compositions contain all of the following weight ratios of octocrylene, octinoxate, octisalate and homosalate:
Octocrylene:Octinoxate:Octisalate:Homosalate: about 4.5: about 2:about 2:about 1.5.

According to preferred embodiments, the at least one metal oxide is present in the composition as a sunscreen active agent. Examples of suitable metal oxides which are sunscreen active agents include physical blockers such as zinc oxide, titanium dioxide, and mixtures thereof.

Other examples of preferred metal oxide sunscreen active agents include pigments or alternatively nanopigments (mean size of the primary particles: generally between 5 nm and 100 µm, preferably between 10 nm and 50 nm) formed from coated or uncoated metal oxides, such as, for example, titanium oxide (amorphous or crystalline in the rutile and/or anatase form), iron oxide, zinc oxide, zirconium oxide or cerium oxide nanopigments. Conventional coating agents of such inorganic sunscreen active agents include alumina and/or aluminium stearate. Examples of nanopigments formed from coated or uncoated metal oxides are disclosed in particular in Patent Applications EP 518 772 and EP 518 773.

According to preferred embodiments, the at least one metal oxide is present in the composition as pigment. Suitable metal oxides can be white or colored, and coated or uncoated.

Specific mention of suitable metal oxides may be made, for example, of inorganic pigments such as titanium dioxide, optionally surface treated, zirconium or cerium oxides and iron or chromium oxides. Specific commercial products: iron oxide containing pigments such as IRON OXIDES (and) DISODIUM STEAROYL GLUTAMATE (and) ALUMINUM HYDROXIDE from Miyoshi Kasei; and titanium oxide containing pigments such as TITANIUM DIOXIDE (and) DISODIUM STEAROYL GLUTAMATE (and) ALUMINUM HYDROXIDE from Miyoshi Kasei.

Preferably, the at least one metal oxide is present in the compositions of the present invention in amounts of active material generally ranging from about 1% to about 50%, preferably from about 5% to about 40%, and more preferably from about 9% to about 30%, by weight, based on the total weight of the composition, including all ranges and subranges in between.

It is to be understood that metal oxides which are sunscreen active agents can also have pigment-like properties, and that metal oxides which are pigments can have sunscreen active agent like properties.

For purposes of this application, a "sunscreen effective amount" of metal oxide in a composition is an amount of metal oxide present which is sufficient to increase the SPF value of the composition by at least 2.

Further, compositions of the present invention are preferably "broad spectrum" compositions. That is, the compositions of the present invention preferably provide protection against both UVA and UVB. Particularly preferred compositions of the present invention are those which (1) do not contain avobenzone; (2) do not contain oxybenzone; and (3) provide protection against UVA by having at least one metal oxide as discussed above in the composition in an amount sufficient to protect keratinous material such as skin from UVA radiation.

Additional Sunscreen Agents

According to preferred embodiments, compositions of the present invention may further comprise one or more additional organic sunscreen active agents.

Organic sunscreens useful herein include anthranilates; cinnamic derivatives; dibenzoylmethane derivatives; salicylic derivatives; camphor derivatives; triazine derivatives, such as those disclosed in Patent Applications U.S. Pat. No. 4,367,390, EP 863 145, EP 517 104, EP 570 838, EP 796 851, EP 775 698, EP 878 469, EP 933 376, EP 507 691, EP 507 692, EP 790 243 and EP 944 624; benzophenone derivatives; β,β-diphenylacrylate derivatives; benzotriazole derivatives; benzalmalonate derivatives; benzimidazole derivatives; imidazolines; bisbenzoazolyl derivatives as disclosed in Patents EP 669 323 and U.S. Pat. No. 2,463,264; p-aminobenzoic acid (PABA) derivatives; methylenebis(hydroxyphenylbenzotriazole) derivatives as disclosed in Applications U.S. Pat. Nos. 5,237,071, 5,166,355, GB 2 303 549, DE 197 26 184 and EP 893 119; screening polymers and screening silicones, such as those disclosed in particular in Application WO 93/04665; dimers derived from α-alkylstyrene, such as those disclosed in Patent Application DE 198 55 649; 4,4-diarylbutadienes as disclosed in Applications EP 0 967 200, DE 197 46 654, DE 197 55 649, EP-A-1 008 586, EP 1 133 980 and EP 133 981; and their mixtures.

By way of illustration, mention may be made, as sunscreens which are generally active in the UV-A and/or UV-B regions, denoted below under their INCI names, of:
p-aminobenzoic acid (PABA) derivatives, in particular PABA, ethyl PABA, ethyl dihydroxypropyl PABA, ethylhexyl dimethyl PABA, glyceryl PABA or PEG-25 PABA,
salicylic derivatives, in particular dipropylene glycol salicylate, or TEA salicylate, dibenzoylmethane derivatives, in particular butyl methoxydibenzoylmethane (sold in particular under the trade name "Parsol 1789"), or isopropyl dibenzoylmethane,
cinnamic derivatives, in particular isopropyl methoxycinnamate, isoamyl methoxycinnamate, cinoxate, DEA methoxycinnamate, diisopropyl methyl cinnamate, or glyceryl ethylhexanoate dimethoxycinnamate,
β,β-diphenylacrylate derivatives, in particular etocrylene,
benzophenone, in particular benzophenone-1, benzophenone-2, benzophenone-3 or oxybenzone, benzophenone-4, benzophenone-5, benzophenone-6, benzophenone-8, benzophenone-9, benzophenone-12, or n-hexyl 2-(4-diethylamino-2-hydroxybenzoyl)benzoate,
benzylidene camphor derivatives, in particular 3-benzylidene camphor, 4-methylbenzylidene camphor, benzylidene camphor sulphonic acid, camphor benzalkonium methosulphate, terephthalylidene dicamphor sulphonic acid (manufactured under the name "Mexoryl SX"), or polyacrylamidomethyl benzylidene camphor (manufactured under the name "Mexoryl SW"),
benzimidazole derivatives, in particular phenylbenzimidazole sulphonic acid, or disodium phenyl dibenzimidazole tetrasulphonate,
triazine derivatives, in particular anisotriazine (sold under the trade name "Tinosorb 8"), ethylhexyl triazone, diethylhexyl butamido triazone, or 2,4,6-tris(diisobutyl 4'-aminobenzalmalonate)-s-triazine,
benzotriazole derivatives, in particular drometrizole trisiloxane or methylene bisbenzotriazolyl tetramethylbutylphenol,
anthranilic derivatives, in particular menthyl anthranilate,
imidazoline derivatives, in particular ethylhexyl dimethoxybenzylidene dioxoimidazoline propionate,
benzalmalonate derivatives, in particular polyorganosiloxane comprising benzalmalonate functional groups,
4,4-diarylbutadiene derivatives, in particular 1,1'-dicarboxy (2,2'-dimethylpropyl)-4,4-diphenylbutadiene, and their mixtures.

Preferred organic sunscreens include phenylbenzimidazole sulphonic acid, benzophenone-3, benzophenone4, benzophenone-5, 4-methylbenzylidene camphor, terephthalylidene dicamphor sulphonic acid, disodium phenyl dibenzimidazole tetrasulphonate, 2,4,6-tris(diisobutyl 4'-aminobenzalmalonate)-s-triazine, anisotriazine, ethylhexyl triazonc, diethylhexyl butamido triazone, methylene bisbenzotriazolyl tetramethylbutylphenol, drometrizole trisiloxane, 1,1'-dicarboxy (2,2'-dimethylpropyl)-4,4-diphenylbutadiene, and their mixtures.

Preferred UVA absorbers generally absorb radiation in the 320 to 400 nm region of the ultraviolet spectrum. Examples of preferred UVA absorbers include anthranilates, benzophenones, and dibenzoyl methanes.

Preferred UVB absorbers generally absorb radiation in the 280 to 320 nm region of the ultraviolet spectrum. Examples of preferred UVB absorbers include camphor derivatives, cinnamates, diphenylacrylates and salicylates.

Specific examples of sunscreen active agents which absorb in the UVA and/or UVB range include:
p-aminobenzoic acid,
oxyethylene (25 mol) p-aminobenzoate,
2-ethylhexyl p-dimethylaminobenzoate,
ethyl N-oxypropylene p-aminobenzoate,
glycerol p-aminobenzoate,
4-isopropylbenzyl salicylate,
methyl diisopropylcinnamate,
isoamyl 4-methoxycinnamate,
diethanolamine 4-methoxycinnamate ate,
3-(4'-trimethylammunium)-benzyliden-bornan-2-one methylsulfate,
2-hydroxy-4-methoxybenzophenone,
2-hydroxy-4-methoxybenzophenone-5-sulfonate,
2,4-dihydroxybenzophenone,
2,2',4,4'-tetrahydroxybenzophenone,
2,2'-dihydroxy-4,4'dimethoxybenzophenone,
2-hydroxy-4-n-octoxybenzophenone,
2-hydroxy4-methoxy-4'-methoxybenzophenone,
-(2-oxoborn-3-ylidene)-tolyl-4-sulfonic acid and soluble salts thereof,
3-(4'-sulfo)benzyliden-bornan-2-one and soluble salts thereof,
3-(4'methylbenzylidene)-d,1-camphor,
3-benzylidene-d,1-camphor,
benzene 1,4-di(3-methylidene-10-camphosulfonic) acid and salts thereof,
urocanic acid,
2,4,6-tris[p-(2'-ethylhexyl-1'-oxycarbonyl)-anilino]-1,3,5-triazine,
2-[(p-(tertiobutylamido)anilino]-4,6-bis-[(p-(2'-ethylhexyl-1'-oxycarbonyl)anilino]-1,3,5-triazine,
2,4-bis{[4-(2-ethyl-hexyloxy)]-2-hydroxy]-phenyl}-6-(4-methoxy-phenyl)-1,3,5-triazine,
the polymer of N-(2 et 4)-[(2-oxoborn-3-yliden)methyl] benzyl]-acrylamide,
1,4-bisbenzimidazolyl-phenylen-3,3',5,5'-tetrasulfonic acid and salts thereof,
the benzalmalonate-substituted polyorganosiloxanes,
the benzotriazole-substituted polyorganosiloxanes (Drometrizole Trisiloxane), dispersed 2,2'-methylene-bis-[6-(2H-benzotriazol-2-yl)-4-(1,1,3,3-tetramethylbutyl)phenol],
solubilized 2,2'-methylene-bis-[6-(2H-benzotriazol-2-yl)-4-(methyl)phenol],
avobenzone,
2-methyldibenzoylmethane,
4-methyldibenzoylmethane,
4-isopropyldibenzoylmethane,
4-tert.-butyldibenzoylmethane,
2,4-dimethyldibenzoylmethane,
2,5-dimethyldibenzoylmethane,
4,4'-diisopropyldibenzoylmethane,
4,4'-dimethoxydibenzoylmethane,
2-methyl-5-isopropyl-4'-methoxydibenzoylmethane,
2-methyl-5-tert.-butyl-4'-methoxydibenzoylmethane,
2,4-dimethyl4'-methoxydibenzoylmethane, and
2,6-dimethyl-4-tert.-butyl-4'-methoxydibenzoylmethane.

Preferably, the additional organic sunscreen active agent(s), if present, are in the compositions according to the invention in amounts ranging from about 1% to about 30% by weight with respect to the total weight of the composition, preferably ranging from about 2 to about 25% by weight with respect to the total weight of the composition, preferably ranging from about 3 to about 20% by weight with respect to the total weight of the composition, including all ranges and subranges therebetween.

Water

According to preferred embodiments, the compositions of the present invention may also contain water. When the compositions of the present invention contain water, they are preferably in the form of an emulsion. Preferably, when the compositions of the present invention contain water, they are in the form of an oil-in-water emulsion (O/W) or a water-in-oil emulsion (W/O). When present, water is preferably present in an amount of from about 25% to about 80% by weight, preferably from about 30% to about 70% by weight, preferably from about 35% to about 65% by weight, including all ranges and subranges therebetween, all weights being based on the total weight of the composition.

The compositions of the present invention may also be anhydrous (that is, contain 2% or less of water, preferably contain 1% or less of water, and preferably contain 0% water).

Optional Ingredients

The compositions of the present invention may also include any one, or more, optional ingredients. Examples thereof include, but are not limited to, co-solvents (volatile and/or non-volatile), surfactants, plasticizers, preservatives, fillers, active ingredients, colorants (dyes), waxes, thickening agents and SPF boosters.

The compositions according to the invention are preferably intended for topical application to keratinous material such as the skin and/or hair. Accordingly, the compositions of the present invention preferably contain a physiologically acceptable medium. Of course, the components of the physiologically acceptable medium of the present invention will depend upon the intended use of the composition as one of ordinary skill in the art would understand that different cosmetic compositions generally contain ingredients useful for the specific type of composition (for example, a shampoo could contain ingredients such as surfactants, a conditioner could contain ingredients such as emollients and/or humectants, a moisturizer could contain ingredients such as emollients, moisturizers and/or active agents, and a sunscreen composition could contain ingredients such as preservatives and SPF boosters, among other things).

Needless to say, the composition of the invention should be cosmetically or dermatologically acceptable, i.e., it should contain a non-toxic physiologically acceptable medium and should be able to be applied to the skin, superficial body growths or the lips of human beings.

According to preferred embodiments of the present invention, methods of increasing the sun protection factor (SPF) properties of a composition comprising adding octocrylene, octinoxate, octisalate, homosalate, to the composition in all of the following weight ratios of octocrylene, octinoxate, octisalate and homosalate:
Octocrylene to Homosalate: from 3:1 to 4.5:1;
Octinoxate to Octisalate: from 1.5:1 to 1:1.5;
Octocrylene to Octinoxate: from 2.5:1 to 1.1:1; and
Octocrylene to Octisalate: from 2.5:1 to 1.25:1.
are provided. According to preferred embodiments, the compositions contain all of the following weight ratios of octocrylene, octinoxate, octisalate and homosalate:
Octocrylene:Octinoxate:Octisalate:Homosalate: about 4.5: about 2:about 2:about 1.5.

According to preferred embodiments of the present invention, methods of increasing the sun protection factor (SPF) properties of a composition comprising adding octocrylene, octinoxate, octisalate, homosalate and at least one metal oxide, to the composition in all of the following weight ratios of octocrylene, octinoxate, octisalate and homosalate:
Octocrylene to Homosalate: from 3:1 to 4.5:1;
Octinoxate to Octisalate: from 1.5:1 to 1:1.5;
Octocrylene to Octinoxate: from 2.5:1 to 1.1:1; and
Octocrylene to Octisalate: from 2.5:1 to 1.25:1.
are provided. According to preferred embodiments, the compositions contain all of the following weight ratios of octocrylene, octinoxate, octisalate and homosalate:
Octocrylene:Octinoxate:Octisalate:Homosalate: about 4.5: about 2:about 2:about 1.5.

According to preferred embodiments of these methods, the at least one metal oxide is selected from the group consisting of zinc oxide, titanium dioxide, and mixtures thereof, and is present in a sunscreen effective amount.

The compositions and methods of the present invention can "comprise," "consist of" or "consist essentially of" the identified ingredients and process steps. For purposes of the compositions and methods of the present invention where the invention "consists essentially of" the identified ingredients and/or process steps, the sole "basic and novel property" of such compositions and/or methods is SPF value. Further, given that it is contemplated that other sunscreen active agents, SPF enhancers and/or SPF boosters (for example, Sunspheres) can be added to the invention methods and compositions in the context of the present invention, a "material effect" on the basic and novel property of the invention can only be an adverse effect. That is, because positive effects on SPF value (such as those effected by additional sunscreen active agents and/or SPF boosters) are within the scope of the present invention, only ingredients which have a material adverse effect on SPF value would be relevant to determining whether or not compositions or methods "consist essentially of" the required elements.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

Example 1—Inventive Compositions of UV Filters

Organic sunscreen active agents were combined with a film former, Dermacryl 79, and dissolved in a solvent, ethanol.

| | |
|---|---|
| Octocrylene | 1-6 wt % |
| OMC | 2-7.5 wt % |
| Octisalate | 2-5 wt % |
| Homosalate | 1-8 wt % |
| Total UV Filters | 10 wt % |
| Film former | 2.5 wt % |
| Ethanol | q.s. |

Sample mixtures of sunscreens were applied to the smoothened side of a PMMA (polymethyl methacrylate)

plate using a draw down bar to control thickness and homogeneity of the film. In vitro SPF was measured using a Labsphere 2000. Each sample was measured at 6 locations per plate on 3 separate plates so an average in vitro SPF value may be obtained for each sunscreen mixture.

Inventive and Comparative Sunscreen Mixtures.*

| Inventive Mixture? | Mean SPF | Wt % ratio Octocrylene: Homosalate | Wt % ratio Octinoxate: Octisalate | Wt % ratio Octocrylene: Octinoxate | Wt % ratio Octocrylene: Octisalate |
|---|---|---|---|---|---|
| Y | 53.28 | 3.00** | 1.00** | 2.25** | 2.25** |
| Y | 50.19 | 4.50** | 0.80** | 2.25** | 1.80** |
| Y | 43.26 | 3.50** | 1.20** | 1.17** | 1.40** |
| Y | 43.00 | 3.50** | 1.25** | 1.40** | 1.75** |
| Y | 42.60 | 3.50** | 1.00** | 1.75** | 1.75** |
| N | 36.63 | 2.00 | 0.57 | 1.50** | 0.86 |
| N | 34.47 | 1.00 | 1.25** | 1.00 | 1.25** |
| N | 34.04 | 1.25 | 0.67** | 1.25** | 0.83 |
| N | 26.66 | 0.43 | 1.25** | 0.60 | 0.75 |
| N | 23.93 | 0.67 | 0.56 | 0.40 | 0.22 |
| N | 23.74 | 1.00 | 1.00** | 0.50 | 0.50 |

*All trials conducted where total sunscreens (Octocrylene, Homosalate, Octinoxate, Octisalate) was 10 wt %.
**wt % ratio falls within the inventive range The results in the above table demonstrate that improved SPF occurs when all four inventive ratios are present.

Example 2—Preparation of Inventive Compositions Comprising Sunscreens and Metal Oxides Octocrylene, octinoxate, octisalate and homosalate, and other organic sunscreen active agents (if present), can be mixed into an oil phase of a formulation, and then combined with metal oxides.

If the final formulation is an emulsion, the emulsion can be formed first with organic sunscreen active agents in the oil phase to create a "white base", at which time the metal oxides can added to the white base. In this scenario, the metal oxides can be added as a separate jet-milled preparation with another powder or filler, added to the white base without any additional ingredients, or added to the white base as a separate multiple-phase or single-phase paste, gel, cream, or suspension.

Alternatively, the metal oxides can be combined with the organic sunscreen active agents prior to forming an emulsion, or during the preparation of the formula, as a single phase preparation.

Example 3—Inventive Composition with Metal Oxides

| Phase | Ingredient | wt % |
|---|---|---|
| A | Solvent | q.s. |
|   | Water-in-oil emulsifiers | 4.50% |
|   | Homosalate | 1.50% |
|   | Ethylhexyl salicylate | 2.00% |
|   | Octocrylene | 4.50% |
|   | Ethylhexyl Methoxycinnamate | 2.00% |
|   | Disteardimonium Hectorite | 0.40% |
|   | Film Former | 5.00% |
| B1 | Water | 35.52% |
|   | Capryly Glycol | 0.55% |
|   | Glycerin | 5.00% |
|   | Dipropylene Glycol | 2.00% |
|   | Preservatives | 0.50% |
|   | Polyacrylate thickener | 3.00% |
| C | Fillers | 4.94% |
|   | Metal Oxide pigments | 9.00% |

The inventive composition containing 10 wt % total organic sunscreens was applied to the roughened side of a PMMA plate with a finger at 2 mg/cm$^2$. The in vitro SPF was measured at 5 locations per plate on 3 separate plates. Average in vitro SPF was 20.07.

Example 4—Inventive Composition with Metal Oxides

| Phase | Ingredient | wt % |
|---|---|---|
| A | Solvent | q.s. |
|   | Water-in-oil emulsifiers | 4.50% |
|   | Homosalate | 1.50% |
|   | Ethylhexyl salicylate | 2.00% |
|   | Octocrylene | 4.50% |
|   | Ethylhexyl Methoxycinnamate | 2.00% |
|   | Disteardimonium Hectorite | 0.40% |
|   | Film Former | 5.00% |
| B1 | Water | 45.52% |
|   | Capryly Glycol | 0.55% |
|   | Glycerin | 5.00% |
|   | Dipropylene Glycol | 2.00% |
|   | Preservatives | 0.50% |
|   | Polyacrylate thickener | 3.00% |
| C | Fillers | 4.94% |
|   | Metal Oxide pigments | 9.00% |

The inventive composition containing 10 wt % total organic sunscreens was tested for in vivo SPF following the 2011 FDA method on 10-subjects and received a label SPF rating of 52.

Example 5—Comparative Composition with Metal Oxides

| Phase | Ingredient | wt % |
|---|---|---|
| A | Solvent | q.s. |
|   | Water-in-oil emulsifiers | 4.50% |
|   | Homosalate | 5.00% |
|   | Ethylhexyl salicylate | 2.50% |
|   | Octocrylene | 2.50% |
|   | Disteardimonium Hectorite | 0.40% |
|   | Film Former | 5.00% |
| B1 | Water | 35.52% |
|   | Capryly Glycol | 0.55% |
|   | Glycerin | 5.00% |
|   | Dipropylene Glycol | 2.00% |
|   | Preservatives | 0.50% |
|   | Polyacrylate thickener | 3.00% |
| C | Fillers | 4.94% |
|   | Metal Oxide pigments | 9.00% |

The comparative composition, using a ratio of sunscreens currently marketed and containing 10 wt % total organic sunscreens was applied to the roughened side of a PMMA plate with a finger at 2 mg/cm$^2$. The in vitro SPF was measured at 5 locations per plate on 3 separate plates. Average in vitro SPF was 7.98, which can be compared to Inventive Example 3, which used the same total wt % of sunscreens with an average in vitro SPF of 20.07.

Example 6—Comparative Composition with Metal Oxides

| Phase | Ingredient | wt % |
|---|---|---|
| A | Solvent | q.s. |
|   | Water-in-oil emulsifiers | 4.50% |
|   | Homosalate | 10.00% |
|   | Ethylhexyl salicylate | 5.00% |
|   | Octocrylene | 5.00% |
|   | Disteardimonium Hectorite | 0.40% |
|   | Film Former | 5.00% |
| B1 | Water | 35.52% |
|   | Capryly Glycol | 0.55% |
|   | Glycerin | 5.00% |
|   | Dipropylene Glycol | 2.00% |
|   | Preservatives | 0.50% |
|   | Polyacrylate thickener | 3.00% |
| C | Fillers | 4.94% |
|   | Metal Oxide pigments | 9.00% |

The comparative composition, using a ratio of sunscreens currently marketed and containing 20 wt % total organic sunscreens was applied to the roughened side of a PMMA plate with a finger at 2 mg/cm$^2$. The in vitro SPF was measured at 5 locations per plate on 3 separate plates. Average in vitro SPF was 13.53, which can be compared to Inventive Example 3, which received a higher average in vitro SPF of 20.07 using half the total wt % of chemical sunscreens.

What is claimed is:

1. A composition comprising octocrylene, octinoxate, octisalate, homosalate, wherein the composition contains all of the following weight ratios:
   octocrylene to homosalate is from about 3:1 to about 4.5:1;
   octinoxate to octisalate is from about 0.8:1 to about 1:1;
   octocrylene to octinoxate is about 2.25:1; and
   octocrylene to octisalate is from about 1.8:1 to about 2.25:1.

2. The composition of claim 1, wherein the composition contains octocrylene to octinoxate to octisalate to homosalate in a weight ratio of about 4.5:about 2:about 2:about 1.5.

3. The composition of claim 1, wherein the composition is an emulsion.

4. The composition of claim 3, wherein the emulsion is a water-in-oil emulsion.

5. The composition of claim 1, wherein the composition is anhydrous.

6. The composition of claim 1, wherein octocrylene, octinoxate, octisalate and homosalate are present in the composition in a combined amount ranging from about 5% to about 15% by weight with respect to the total weight of the composition.

7. A composition comprising octocrylene, octinoxate, octisalate, homosalate and at least one metal oxide, wherein the composition contains all of the following weight ratios:
   octocrylene to homosalate is from about 3:1 to about 4.5:1;
   octinoxate to octisalate is from about 0.8:1 to about 1:1;
   octocrylene to octinoxate is about 2.25:1; and
   octocrylene to octisalate is from about 1.8:1 to about 2.25:1.

8. The composition of claim 7, wherein the composition contains octocrylene to octinoxate to octisalate to homosalate in a weight ratio of about 4.5:about 2:about 2:about 1.5.

9. The composition of claim 7, wherein the composition is an emulsion.

10. The composition of claim 9, wherein the emulsion is a water-in-oil emulsion.

11. The composition of claim 7, wherein the composition is anhydrous.

12. The composition of claim 7, wherein octocrylene, octinoxate, octisalate and homosalate are present in the composition in a combined amount ranging from about 5% to about 15% by weight with respect to the total weight of the composition.

13. The composition of claim 7, wherein the at least one metal oxide is selected from the group consisting of zinc oxide, titanium dioxide, and mixtures thereof, and wherein the at least one metal oxide is present in a sunscreen effective amount.

14. A method of improving sun protection factor properties in a composition comprising adding octocrylene, octinoxate, octisalate, homosalate, to the composition in all of the following weight ratios of octocrylene, octinoxate, octisalate and homosalate:
   octocrylene to homosalate is from about 3:1 to about 4.5:1;
   octinoxate to octisalate is from about 0.8:1 to about 1:1;
   octocrylene to octinoxate is about 2.25:1; and
   octocrylene to octisalate is from about 1.8:1 to about 2.25:1.

15. The method of claim 14, wherein the composition contains octocrylene to octinoxate to octisalate to homosalate in a weight ratio of about 4.5:about 2:about 2:about 1.5.

16. The method of claim 14, wherein the composition is an emulsion.

17. The method of claim 15, wherein the emulsion is a water-in-oil emulsion.

18. The method of claim 14, wherein the composition is anhydrous.

19. The method of claim 14, wherein octocrylene, octinoxate, octisalate and homosalate are present in the composition in a combined amount ranging from about 5% to about 15% by weight with respect to the total weight of the composition.

20. The method of claim 14, wherein the composition further comprises at least one metal oxide.

* * * * *

UNITED STATES PATENT AND TRADEMARK OFFICE
CERTIFICATE OF CORRECTION

| | | |
|---|---|---|
| PATENT NO. | : 9,693,943 B1 | Page 1 of 1 |
| APPLICATION NO. | : 14/985168 | |
| DATED | : July 4, 2017 | |
| INVENTOR(S) | : Brian Scott Bodnar et al. | |

It is certified that error appears in the above-identified patent and that said Letters Patent is hereby corrected as shown below:

On the Title Page

Item (65) omitted, should read:
--Prior Publication Data US 2017/0189291 A1 July 06, 2017--.

Signed and Sealed this
Tenth Day of April, 2018

Andrei Iancu
*Director of the United States Patent and Trademark Office*